United States Patent [19]

Suzuki et al.

[11] Patent Number: 5,318,970
[45] Date of Patent: Jun. 7, 1994

[54] ISOXAZOLE COMPOUNDS, PHARMACEUTICALLY ACCEPTABLE SALTS THEREOF AND MEDICAL USES THEREOF

[75] Inventors: Masahiro Suzuki; Kenji Nozaki, both of Hannou; Makoto Kajitani, Irumagun; Mitsugi Yasumoto, Honjo; Naohiko Ono; Takashi Shindo, both of Tokushima, all of Japan

[73] Assignee: Taiho Pharmaceutical Co., Ltd., Tokyo, Japan

[21] Appl. No.: 844,561

[22] PCT Filed: Sep. 20, 1991

[86] PCT No.: PCT/JP91/01253
§ 371 Date: Mar. 17, 1993
§ 102(e) Date: Mar. 17, 1993

[87] PCT Pub. No.: WO92/05162
PCT Pub. Date: Apr. 2, 1992

[30] Foreign Application Priority Data

Sep. 21, 1990 [JP] Japan ................ 2-253184

[51] Int. Cl.$^5$ ............... A61K 31/495; C07D 413/12; C07D 413/14; C07D 413/06
[52] U.S. Cl. ..................... 514/252; 544/295; 544/367; 544/373; 544/374; 544/391; 544/399; 544/402; 548/247
[58] Field of Search ............ 544/295, 367; 514/252

[56] References Cited

U.S. PATENT DOCUMENTS

| | | | |
|---|---|---|---|
| 3,642,812 | 2/1972 | Southern | 548/247 |
| 4,327,222 | 4/1982 | Micetich et al. | 548/247 |
| 5,182,284 | 1/1993 | Suzuki et al. | 514/255 |
| 5,229,386 | 7/1993 | Takasugi et al. | 514/236.8 |

FOREIGN PATENT DOCUMENTS

| | | |
|---|---|---|
| 59764 | 5/1981 | Japan . |
| 75471 | 4/1985 | Japan . |
| 223568 | 9/1990 | Japan . |

*Primary Examiner*—Emily Bernhardt
*Attorney, Agent, or Firm*—Nikaido, Marmelstein, Murray & Oram

[57] ABSTRACT

A isoxazole compound represented by the formula (1):

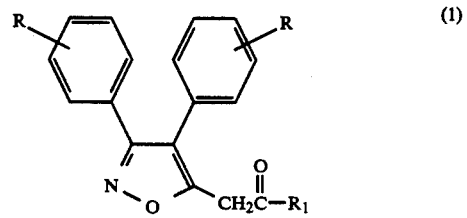

(1)

wherein R represents a hydrogen atom or a lower alkoxy group, $R_1$ is a group represented by the formula (2):

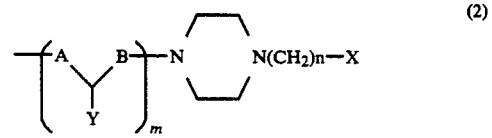

(2)

(wherein A represents —NH— or —O—, B represents a methylene group or a carbonyl group, m is 0 or 1, n is an integer of 1 to 12, X represents a hydrogen atom, a hydroxy group or a lower alkoxycarbonyl group, Y represents a phenyl group which can be substituted with one or more halogen atoms, or a hydrogen atom), a group represented by the formula (3):

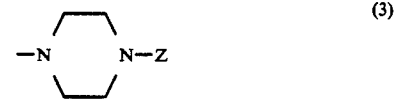

(3)

(wherein Z represents a pyrimidinyl group), or a group represented by the formula (4):

(Abstract continued on next page.)

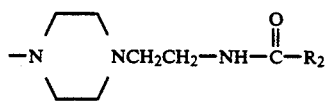
(wherein $R_2$ represents a styryl group which can be substituted with one or more hydroxy groups); a pharmaceutically acceptable salt thereof; or a medical use thereof in a method of inhibiting lipoxygenase, inhibiting 5-lipoxygenase or inhibiting cyclooxygenase.
11 Claims, No Drawings

ISOXAZOLE COMPOUNDS, PHARMACEUTICALLY ACCEPTABLE SALTS THEREOF AND MEDICAL USES THEREOF

FIELD OF THE INVENTION

The present invention relates to novel isoxazole compounds having a lipoxygenase inhibiting activity and a cyclooxygenase inhibiting activity, pharmaceutically acceptable salts thereof and medical uses thereof.

BACKGROUND OF THE INVENTION

It is considered that leukotrienes produced by 5-lipoxygenase from arachidonic acid, and prostaglandins produced by cyclooxygenase from arachidonic acid are deeply concerned in a crisis of allergic asthma, allergic rhinitis, inflammation, etc. Consequently it is desired to inhibit both 5-lipoxygenase and cyclooxygenase in order to strongly and properly inhibit various allergic diseases, inflammations and other diseases. The development of a drug inhibiting both enzymes is earnestly desired.

DISCLOSURE OF THE INVENTION

The present inventors have conducted a research in considering the foregoing problems in the background, and found that novel isoxazole compounds as indicated in the following formula (1) and pharmaceutically acceptable salts thereof have an excellent lipoxygenase inhibiting activity and an excellent cyclooxygenase inhibiting activity, and are useful as a drug. Thus, the present invention has been accomplished.

The present invention provides isoxazole compounds, pharmaceutically acceptable salts thereof, the compounds which are represented by the formula (1):

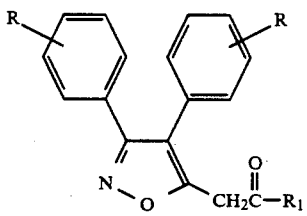

wherein R represents a hydrogen atom or a lower alkoxy group, $R_1$ is a group represented by the formula (2):

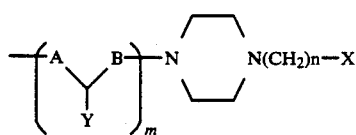

(wherein A represents —NH— or —O—, B represents a methylene group or a carbonyl group, m is 0 or 1, n is an integer of 1 to 12, X represents a hydrogen atom, a hydroxy group or a lower alkoxycarbonyl group, Y represents a phenyl group which can be substituted with one or more halogen atoms, or a hydrogen atom), a group represented by the formula (3):

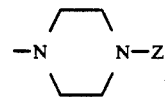

(wherein Z represents a pyrimidinyl group), or a group represented by the formula (4):

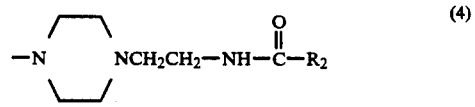

(wherein $R_2$ a styryl group which can be substituted with one or more hydroxy groups).

The compounds of the present invention represented by the formula (1) has an excellent lipoxygenase inhibiting activity and cyclooxygenase inhibiting activity. Examples of lipoxygenases are 5-lipoxygenase, 12-lipoxygenase and 15-lipoxygenase, etc. The compounds of the invention exhibit, in particular, a potent activity of 5-lipoxygenase inhibition.

The compounds of the invention have a high lipoxygenase inhibitory effect and cyclooxygenase inhibitory effect, and are useful as an anti-asthmatic agent, anti-allergic agent, agent for treating encephalopathy, cardiovascular agent, agent for treating nephritis, anti-inflammatory analgesic agent, anti-rheumatic agent, agent for treating dermatosis such as psoriasis and liver disease agent.

Accordingly, the present invention provides an anti-asthmatic agent, anti-allergic agent, agent for treating encephalopathy, cardiovascular agent, agent for treating nephritis, anti-inflammatory analgesic agent, anti-rheumatic agent, agent for treating dermatosis such as psoriasis and liver disease agent, the agents each comprising an effective amount of the compound of the formula (1) or a pharmaceutically acceptable salt thereof, and a pharmaceutical carrier.

The present invention provides a method for treating asthma, allergy, encephalopathy, circulatory diseases, nephritis, inflammation, rheumatism, dermatosis such as psoriasis and liver disease, characterised in that an effective amount of the compound of the formula (1) or a pharmaceutically acceptable salts thereof are administered to a patient.

When the compounds represented by the formula (1) have an asymmetric carbon atom, the isoxazole compounds of the invention include R form, S form and a mixture of R form and S form in any rate.

Examples of a lower alkoxy group represented by R and of a lower alkoxy groups of a lower alkoxycarbonyl group represented by X in the present invention are straight- or branched-chain alkoxy groups having 1 to 4 carbon atoms, such as methoxy group, ethoxy group, n-propoxy group, isopropoxy group, n-butoxy group, isobutoxy group, sec-butoxy group and t-butoxy group.

Examples of halogen atoms as substituents for the phenyl group represented by Y are fluorine atom, chlorine atom, bromine atom, iodine atom, etc.

The phenyl group which can be substituted with halogen atoms has 1 to 5, preferably 1, 2 or 3 halogen atoms.

In addition, examples of styryl groups which can be substituted with one or more hydroxy groups and which are represented by $R_2$ in formula (4) are styryl groups having 1 to 5, preferably 1 to 3 hydroxy groups on benzene ring.

Examples of pharmaceutically acceptable salts of the isoxazole compounds of the invention are salts prepared using an inorganic acid such as hydrochloric acid, sulfuric acid, phosphoric acid or the like, or an organic acid such as maleic acid, succinic acid, malic acid, oxalic acid, fumaric acid or the like.

In said compounds represented by the formula (1), R is preferably a lower alkoxy group, more preferably a methoxy group.

$R_1$ is preferably a group represented by the formula (2), more preferably a group represented by the formula (2) wherein A represents —NH— or —O—, B represents a methylene group or a carbonyl group, m is 1, n is an integer of 6 to 12, X represents a hydrogen atom or a hydroxy group, Y represents a phenyl group or a hydrogen atom, most preferably a group represented by the formula (2) wherein A represents —NH—, B represents a methylene group or a carbonyl group, m is 1, n is 10, X represents a hydrogen atom or a hydroxy group, and Y represents a phenyl group or a hydrogen atom.

- Of the compounds represented by the formula (1), preferable compounds are those wherein R represents a lower alkoxy group and $R_1$ represents the compound of the formula (2) (wherein A represents —NH— or —O—, B represents a methylene group or a carbonyl group, m is 1, n is an integer of 6 to 12, X represents a hydrogen atom or a hydroxy group and Y represents a phenyl group or a hydrogen atom).

The most preferable compounds are those wherein R represents a methoxy group and $R_1$ represents the compound of the formula (2) (wherein A represents —NH—, B represents a methylene group or a carbonyl group, m is 1, n is 10, X represents a hydrogen atom or a hydroxy group and Y represents a phenyl group or a hydrogen atom).

The compounds of the formula (1) according to the invention is generally prepared by the process illustrated below in Reaction Scheme (i):

<Reaction Scheme (i)>

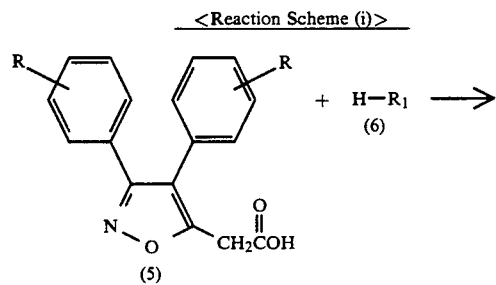

-continued
<Reaction Scheme (i)>

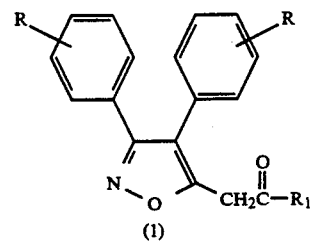

wherein R and $R_1$ are as defined above.

The desired isoxazole compound of the formula (1) is prepared by reacting a carboxylic acid of the formula (5) with an amine or alcohol compound of the formula (6) in a solvent using a condensing agent in the presence or absence of a base.

If the compound represented by the formula (6) has a hydroxy group not to be participate in the reaction, the condensation reaction can be performed after protecting the hydroxy group with a suitable protective group. Useful protective groups are not specifically limited insofar as the protective groups used do not adversely affect others when said protective group is removed by deprotection. Examples of protective groups are methoxyethoxymethyl group, methoxymethyl group, tetrahydrofuranyl group, tetrahydropyranyl group, etc. These protective groups can be introduced by the conventional methods, such as the method disclosed in Journal of American Chemical Society, 100, 8031 (1978).

Solvents in the condensation reaction are not specifically limited insofar as they do not participate in the reaction. Useful solvents include, for example, ether, tetrahydrofuran and like ethers, methylene chloride, chloroform and like halogenated hydrocarbons, benzene, toluene and like aromatic hydrocarbons, N,N-dimethylformamide, dimethylsulfoxide, acetonitrile and like aprotic polar solvents, etc. Useful condensing agents include, for example, N,N'-dicyclohexylcarbodiimide, 1-ethyl-3-(3-dimethylaminopropyl)carbodiimide, ethoxycarbonyl chloride, trimethylacetyl chloride, carbonyldiimidazole, 2-chloro-1-methylpyridinium iodide, 2-chloro-1-methylpyridinium p-toluenesulfonate, 1,3-thiazolidine-2-thione, etc. Useful bases include, for example, 4-dimethylaminopyridine, 1-hydroxybenzotriazole, pyridine, triethylamine, diisopropylethylamine, etc. In the reaction, it is preferable to use, per equivalent of the compound of the formula (6), about 1 to 2 equivalents of the compound of the formula (5), about 1 to 3 equivalents of the condensing agent and a catalytic amount or about 1 to 2 equivalents of the base. The reaction time is about 2 to 48 hours. The reaction advantageously proceeds if conducted at a temperature between ice cooling temperature and reflux temperature of the solvent.

The compound of the formula (1) according to the invention, wherein $R_1$ is a group represented by the formula (4), can be also prepared by the process illustrated below in Reaction Scheme (ii):

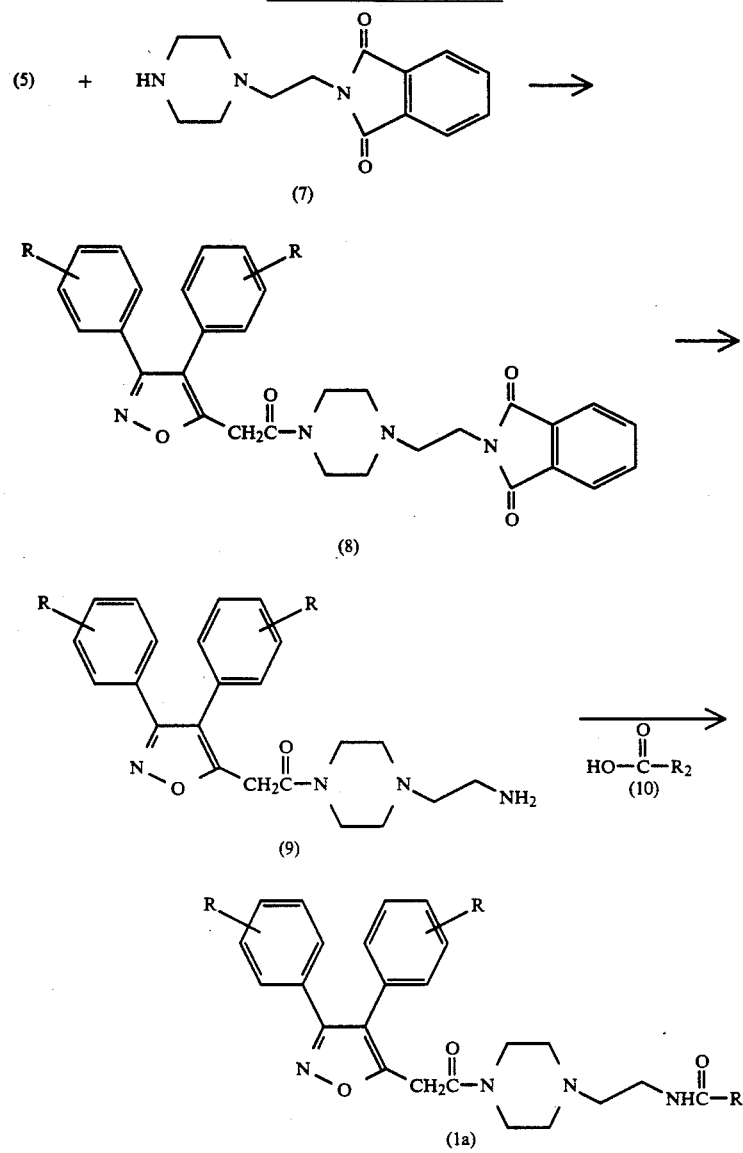

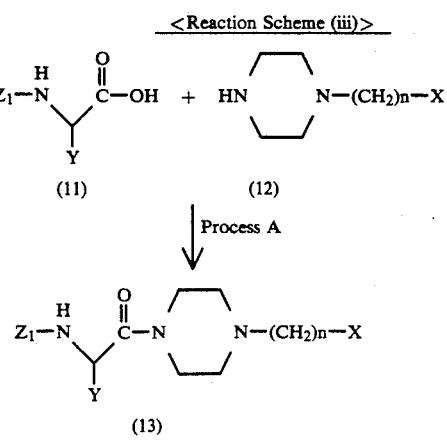

wherein R and $R_2$ are as defined above.

First, a compound of the formula (8) is prepared by reacting a carboxylic acid of the formula (5) with a known compound of the formula (7) in the same way as in Reaction Scheme (i). Second, the compound of the formula (8) thus obtained is converted to a compound of the formula (9) for example, by removing a protective group according to the conventionally used Gabriel reaction. Finally, the desired isoxazole compound of the formula (1a) is prepared by reacting the compound of the formula (9) with a carboxylic acid of the formula (10) in the same way as in Reaction Scheme (i).

A compound of the formula (6) (wherein $R_1$ represents a compound of the formula (2)) used as a starting material of the Reaction Scheme (i) is prepared according to the Reaction Scheme (iii) below. In contrast, the compound of the formula (6) (wherein $R_1$ represents a compound of the formula (2), m is 1, and A is —O—) can be prepared according to the method disclosed in Japanese Unexamined Patent Publication No. 61-152656. The compound of the formula (6) wherein $R_1$ represents a compound of the formula (3) is a known compound:

-continued
<Reaction Scheme (iii)>

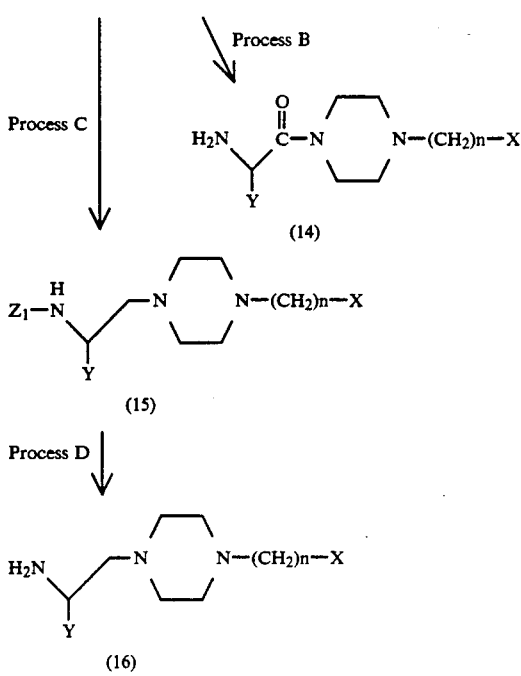

wherein $Z_1$ represents a t-butoxycarbonyl group or a benzyloxycarbonyl group, and X, Y and n are as defined above.

Reaction scheme (iii) contains two routes. One is a route to prepare a compound (14) by producing condensation product (13) according to (Process A), followed by deprotecting the compound (13) according to (Process B). The other is a route to prepare a compound (16) by reducing the condensation product (13) according to (Process C), followed by deprotection of the reducing product according to (Process D).

The (Process A) to (Process D) will be described below in this sequence.

Process A

A piperazine compound of the formula (13) is obtained by reacting the known carboxylic acid of the formula (11) with the known amine of the formula (12) in the same way as reaction scheme (i).

Process B

The compound of the formula (13) is treated with an acid or hydrogenated in a solvent to remove the group $Z_1$, whereby the piperazine compound of the formula (14) is produced. Useful solvents are not specifically limited insofar as they do not participate in the reaction. Examples of solvents are methanol, ethanol and like protic polar solvents as well as the solvents as shown in reaction scheme (i). Useful acid are not specifically limited insofar as they are those commonly employed in removing the protective groups of amino groups. Examples of useful acids are hydrochloric acid, sulfuric acid, trifluoroacetic acid, hydrobromic acid, etc. When hydrogenation is effected to remove the protective group, use of a catalyst such as palladium carbon or the like enables the reaction to advantageously proceed. The conditions for removing protective group are those already known or conventionally employed, for example, in removing the protective groups in the synthesis of polypeptides.

Process C

The compound of the formula (13) is reacted with a reducing agent in a solvent, whereby the piperazine compound of the formula (15) is produced. Useful solvents are not specifically limited insofar as they do not participate in the reaction. For example, the solvents exemplified above for use in reaction scheme (i) can be used. The reaction time is about 2 to 48 hours, and the reaction is conducted with ice cooling. Useful reducing agents include lithium aluminum hydride, aluminum hydride, etc. Such reducing agent is usually used in an amount of about 2 to 10 equivalents per equivalents of the compound of the formula (13) or an excessive amount.

Process D

The compound of the formula (15) is reacted in the same way as (Process B), whereby the piperazine compound of the formula (16) is produced.

Reference Examples 1 to 6 to be described later specifically illustrate the preparation of starting compounds according to (Process A) to (Process D).

The compound of the formula (6) wherein $R_1$ is a group represented by the formula (4), used as a starting material in the Reaction Scheme (i) can be prepared according to the following Reaction Scheme (iv):

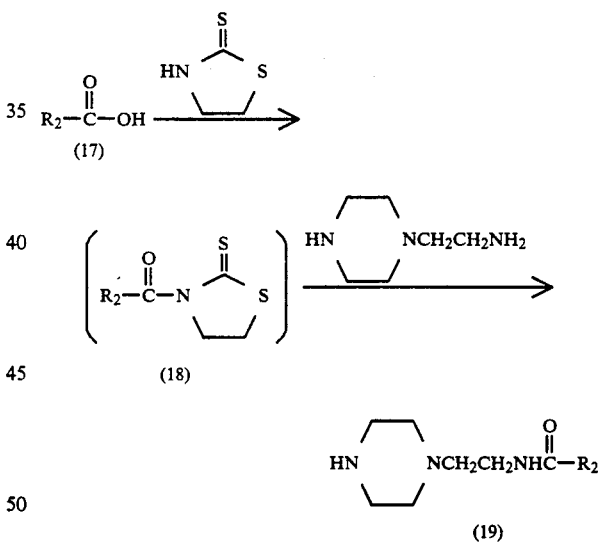

wherein $R_2$ is as defined above.

An intermediate of the formula (18) is produced by reacting the carboxylic acid of the formula (17) with 1,3-thiazolidine-2-thione in a solvent using a condensing agent in the presence of a catalyst. Without isolating the compound (18), N-(β-aminoethyl) piperazine is added to the reaction mixture to obtain the desired compound of the formula (19). Solvents useful in the condensation reaction are not specifically limited insofar as they do not participate in the reaction. Useful solvents include, for example, ether, tetrahydrofuran and like ethers, methylene chloride, chloroform and like halogenated hydrocarbons, benzene, toluene and like aromatic hydrocarbons, etc. Useful condensing agents include, for example, N,N'-dicyclohexylcarbodiimide, ethoxycarbonyl chloride, etc. Useful catalysts include, for example, 4-dimethylamino pyridine, 1-hydroxybenzotriazole, triethylamine, pyridine, etc. In the reaction, it is preferable to use, per equivalent of the carboxylic acid of the formula (17), about 1 to 1.5 equivalents of 1,3-thiazolidine-2-thione, about 1 to 2 equivalents of the condensing agent, about 0.1 to 1.5 equivalents of the catalyst and about 1 to 2 equivalents of N-($\beta$-aminoethyl) piperadine. The reaction advantageously proceeds if conducted at a temperature between ice cooling temperature and room temperature. The reaction time is about 1 to 4 hours in the reaction of the carboxylic acid and 1,3-thiazolidine-2-thione, and about 1 to 48 hours in the reaction of the intermediate and N-($\beta$-aminoethyl) piperazine.

The compounds of the invention prepared by the foregoing reactions can be converted into salts thereof according to a conventional method, for example, by treating the compounds with the foregoing organic or inorganic acids in a solvent such as ethers, lower alcohols, ethyl acetate, hexane or the like at approximately room temperature.

The compounds obtained in Reaction Schemes (i) to (iv) can be isolated and purified by usual means conventionally employed in the art such as concentration, filtration, recrystalization, various types of chromatography, etc.

For use as medicaments, the compounds of the present invention can be made into various pharmaceutical dosage forms according to a preventive or therapeutic purpose. Examples of pharmaceutical dosage forms are oral preparations, injections, suppositories and so on. Such preparations can be formulated in a manner already known or conventional to those skilled in the art.

For the formulation of solid preparations for oral administration, an excipient and, when required, a binder, disintegrator, lubricant, coloring agent, corrigent, flavor, etc. are added to the compound of the invention, and then a preparation is formulated in a usual way as tablets, coated tablets, granules, powders, capsules, or the like. Such additives are those already known in the art, and useful examples are excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dried starch, sodium alginate, agar powder, sodium hydrogencarbonate, calcium carbonate, sodium lauryl sulfate, stearic acid monoglyceride and lactose; lubricants such as purified talc, stearic acid salt, borax and polyethylene glycol; corrigents such as sucrose, bitter orange peel, citric acid and tartaric acid, etc.

For the formulation of liquid preparations for oral administration, a corrigent, buffer, stabilizer, flavor, etc. can be added to the compound of the present invention, and the mixture can be formulated in a usual way into an oral liquid preparations, syrup, elixir or the like. Examples of useful corrigents are those exemplified above. Examples of buffers are sodium citrate, etc. Examples of stabilizers are tragacanth, gum arabic, gelatin, etc.

Injections can be prepared as a subcutaneous, intramuscular or intravenous injection in a conventional way by adding to the compound of the invention a pH adjusting agent, buffer, stabilizer, isotonic agent, local anesthetic, etc. Examples of pH adjusting agents and buffers are sodium citrate, sodium acetate, sodium phosphate, etc. Examples of stabilizers are sodium pyrosulfite, EDTA, thioglycolic acid, thiolactic acid, etc. Examples of local anesthetics are procaine hydrochloride, lidocaine hydrochloride, etc.

Suppositories can be prepared in a usual manner by adding to the compound of the invention a pharmaceutically acceptable carrier already known in the art, such as polyethylene glycol, lanolin, cacao fat and oil, fatty acid triglyceride and, if desired, a surfactant, for example, Tween (registered trademark).

The amount of the compound of the present invention to be incorporated into each of the dosage units varies with the symptoms of the patient or with the type of the preparations. The preferable amount per administartion unit is about 1 to 1,000 mg for oral preparations, about 0.1 to 500 mg for injections, or about 5 to 1,000 mg for suppositories. The dosage per day of the drug in the above dosage forms is variable with the symptoms, body weight, age, sex and other factors of the patient, but usually ranges from about 0.1 to 5,000 mg, preferably from about 1 to 1,000 mg for human adult. The preparation is preferably administered in a single dose or in two to four devided doses.

BEST MODE TO CARRY OUT THE INVENTION

The present invention will be described below in more detail with reference to the following Reference Examples, Examples, Formulation Examples and Pharmacological Test Examples.

REFERENCE EXAMPLE 1

Synthesis of 1-(2-amino-2-phenylacetyl)-4-decylpiperazine (a) 20 g (0.18 mole) quantity of N-formylpiparazine, 37.2 ml (0.18 mole) of 1-bromodecane and 25g (0.18 mole) of potassium carbonate were suspended in 20 ml of N,N-dimethylformamide and the suspension was stirred at 80° C for 3 hours. The reaction mixture was further extracted with 300 ml of benzene, and the benzene layer was washed with water, dried over anhydrous magnesium sulfate and concentrated under reduced pressure. The residue was dissolved in 80 ml of methanol, and 20 ml of concentrated hydrochloric acid was added thereto and the mixture was refluxed for 3 hours. The solvent was evaporated under reduced pressure and the precipitated crystals were washed with acetone, giving 35.6 g (yield: 66%) of N-decylpiperadine as a hydrochloride.

(b) 2.3 g (8.64 mmole) quantity of N,N'-dicyclohexylcarbodiimide was added to 20 ml of a solution of 2.0 g (7.35 mmole) of N-decylpiperazine hydrochloride, 1.9 g (7.56 mmole) of N-t-butoxycarbonylphenylglycine, 1.3 g (15.5 mmole) of sodium hydrogencarbonate and 122 mg (1.0 mmole) of 4-dimethylaminopyridine in anhydrous methylene chloride. The mixture was stirred at room temperature for 12 hours. The precipitated crystals were collected by filtration and washed with methylene chloride. Mother liquor and the washings were combined and concentrated under reduced pressure and the residue was purified by silica gel chromatography (chloroform : methanol = 15 : 1), giving 2.8 g (yield: 83 %) of 1-(N-t-butoxycarbonyl-phenylglycyl)-4-decyl-piperazine.

$^1$H-NMR (CDCl$_3$)$\delta$: 0.87 (3H, m), 1.24–1.41 (25H, m), 2.14–2.39 (6H, m), 3.30–3.68 (4H, m), 5.55 (1H, d, J=7.1 Hz), 6.12 (1H, d, J=7.1 Hz), 7.23–7.33 (5H, m).

MS: 460 (M+1).

(c) 2.9 g (6.32 mmole) quantity of 1-(N-t-butoxycarbonylphenylglycyl)-4-decylpiperazine was dissolved in 5 ml of ethyl acetate, and 20 ml of 4N hydrochloric acid-ethyl acetate solution was added thereto with ice-cooling and the mixture was stirred for 1 hour. The precipitated crystals were collected by filtration, washed with a small quantity of ether and dried under reduced pressure, giving 2.5 g (yield: 90 %) of 1-(2-amino-2-phenylacetyl)-4-decylpiperazine as a hydrochloride.

$^1$H-NMR (DMSO-d$_6$+D$_2$O)$\delta$: 0.86 (3H, m), 1.27 (12H, m), 1.76 (2H, m), 3.11–3.54 (12H, m), 4.72 (1H, m), 7.40–7.57 (5H, m).

MS: 358 (M−1).

REFERENCE EXAMPLE 2

Synthesis of 1-(2-aminoacetyl)-4-decylpiperazine

The same procedure as in Reference Example 1 was repeated with the exception of using N-t-butoxycarbonylglycine in place of N-t-butoxycarbonylphenylglycine, giving 1-(2-aminoacetyl)-4-decylpiperazine as a hydrochloride in a yield of 76 %.

$^1$H-NMR (DMSO-d$_6$+D$_2$O)$\delta$: 0.86 (3H, m), 1.26 (12H, m), 1.72 (2H, m), 3.09–4.52 (14H, m).

MS: 283 (M+).

REFERENCE EXAMPLE 3

Synthesis of 1-(2-amino-2-phenylethyl)-4-decylpiperazine

A solution of 17 g (37 mmole) of 1-(N-t-butoxycarbonylphenylglycyl)-4-decylpiperazine obtained in the same way as in Reference Example 1 (b) in 50 ml of tetrahydrofuran was added dropwise with ice-cooling to 140 ml of a tetrahydrofuran solution of aluminum hydride (0.66 mmole/ml solution) [Journal of American Chemical Society, 90, 2927 (1968)], and the mixture was stirred for 3 hours. To the solution thus obtained was added dropwise a solution of 2.1 g of potassium hydroxide in 7.6 ml of water and the mixture was stirred at room temperature for 12 hours. The precipitate was collected by filtration and washed with 100 ml of tetrahydrofuran. The mother liquor and the washings were combined and concentrated under reduced pressure. The residue was dissolved in 150 ml of ethyl acetate and the solution was washed sequentially with 80 ml of 0.5 N hydrochloric acid, an aquaous solotion of saturated sodium hydrogencarbonate and a brine. The resulting solution was dried over anhydrous magnesium sulfate and concentrated under reduced pressure. The residue was treated in the same way as in Reference Example 1 (c), giving 9.9 g (yield: 59 %) of 1-(2-amino-2-phenylethyl)-4-decylpiperazine as a hydrochloride.

$^1$H-NMR (DMSO-d$_6$+D$_2$O)$\delta$: 0.86 (3H, m), 1.26 (12H, m), 1.70 (2H, m), 2.98–3.86 (14H, m), 4.72 (1H, m), 7.40–7.63 (5H, m).

MS: 344 (M−1).

REFERENCE EXAMPLE 4

Synthesis of 1-(2-aminoethyl)-4-decylpiperazine 1-(N-t-Butoxycarbonylglycyl)-4-decylpiperazine obtained as an intermediate in Reference Example 2 was treated in the same way as in Reference Example 3, giving 1-(2-aminoethyl)-4-decylpiperazine as a hydrochloride in a yield of 65 %.

$^1$H-NMR (DMSO-d$_6$+D$_2$O)$\delta$: 0.84 (3H, m), 1.27 (14H, m), 1.74 (2H, m), 3.15–3.51 (14H, m).

MS: 269 (M+)

REFERENCE EXAMPLE 5

Synthesis of 1-(2-amino-2-phenylethyl)-4-[10-(2-tetrahydropyranyloxy)decyl]piperazine 583 mg (1.40 mmole) quantity of 1-benzyl-4-[10-(2-tetrahydropyranyloxy)decyl]piperazine was dissolved in 20 ml of ethanol, and 200 mg of 10 % palladium-carbon was added thereto and the mixture was shaken at 3 atm. for 8 hours under hydrogen atmosphere. The catalyst was filtered off and the filtrate was evaporated under reduced pressure to dryness, giving 375 mg (yield: 82 %) of N-[10-(2-tetrahydropyranyloxy)decyl]-piperazine. Then, using N-t-butoxycarbonylphenylglycine and N-[10-(2-tetrahydropyranyloxy)decyl]piperazine was treated in the same procedure as in Reference Examples 1 and 3, giving 384 mg (yield: 75 %) of 1-(2-amino-2-phenylethyl)-4-[10-(2-tetrahydropyranyloxy)-decyl]piperazine as a hydrochloride.

$^1$H-NMR (CDC$_3$+D$_2$O)$\delta$: 1.28–1.63 (20H, m), 2.19–2.68 (14H, m), 3.25–3.86 (5H, m), 4.56 (1H, m), 7.24–7.38 (5H, m).

MS: 444 (M−1), 428(M−17)

REFERENCE EXAMPLE 6

Synthesis of 11-(1-piperazinyl)undecanoic acid methyl ester 26.5 g (0.1 mole) quantity of 11-bromoundecanoic acid was dissolved in 300 ml of methanol, and 5 to 6 drops of sulfuric acid was added thereto and the mixture was stirred at room temperature for 24 hours and concentrated. 500 ml quantity of ethyl acetate was added to the residue and the solution was washed sequentially with 100 ml of water and 100 ml of a brine, and then dried over anhydrous magnesium sulfate. Ethyl acetate was evaporated under reduced pressure and the residue was dissolved in 200 ml of dimethylformamide. To the solution were added 11.4 g (0.1 mole) of formylpiperazine and 18.5 g (0.22 mole) of sodium hydrogencarbonate. The mixture was stirred at 80 ° C for 3 hours and concentrated under reduced pressure. 500 ml quantity of ethyl acetate was added to the residue and the mixture was washed sequentially with 100 ml of water and 100 ml of a brine, and then dried over anhydrous magnesium sulfate. Ethyl acetate was evaporated under reduced pressure. To the residue were added 300 ml of methanol and 50 ml of concentrated hydrochloric acid, and the mixture was refluxed for 3 hours. The solvent was evaporated under reduced pressure and the precipitated white crystals were washed with acetone, giving 25 g (yield: 70 %) of 11-(1-piperazinyl)undecanoic acid methyl ester as a hydrochloride.

$^1$H-NMR (DMSO-d$_6$+D$_2$O)$\delta$: 1.00–1.94 (18H, m), 2.54 (2H, m), 3.14 (2H, m), 3.47 (6H, m), 3.57 (3H, s).

MS: 284 (M+).

EXAMPLE 1

447 mg (1.0 mmole) quantity of 1-(2-hydroxy-2-phenylethyl)-4-[10-(2-tetrahydropyranyloxy)decyl]piperazine, 697 mg (2.0 mmole) of 3,4-bis-(p-methoxyphenyl)isoxazole-5-acetic acid and a catalytic amount of 4-dimethylaminopyridine were dissolved in acetonitrile (20 ml), and an acetonitrile (20 ml) solution of N,N'- dicyclohexylcarbodiimide (575 mg, 3.0 mmole) was added dropwise to the mixture with ice-cooling, and then the mixture was stirred at room temperature for 6 hours. The reaction mixture was evaporated under reduced pressure to remove the solvent, and the residue was purified by silica gel column chromatography (chloroform : methanol =20 : 1). The protected product obtained was dissolve in 2-propanol (30 ml), and maleic acid (235mg) was added thereto. After refluxing the solution for 12 hours, the solvent was evaporated under reduced pressure. 1N-sodium hydroxide aquaous solution (50 ml) was added to the residue, and the mixture was extracted with chloroform (100 ml). The chloroform layer was dried over anhydrous magnesium sulfate and then concentrated under reduced pressure. The residue was purified by silica gel column chromatography (chloroform:methanol=5:1). The resulting oil was dissolved in ether (20 ml), and an ether (30 ml) solution of maleic acid (140 mg) was added thereto. The precipitated crystals were collected by filtration, washed with a small amount of ether and dried under reduced pressure to give 559 mg (yield: 61 %) of compound 1 described in Table 1.

EXAMPLE 2

Compounds 2 to 11 and 13 shown below in Table 1 were prepared in the same way as in Example 1. Among the elemental analysis data shown in Table 1, values found by the analysis are described in the upper position, and theoretical values are described in the lower position.

EXAMPLE 3

3,4-Bis-(p-methoxyphenyl) isoxazole-5-acetic acid (1.4 g, 4.0 mmole), N-(2-piperazinylethyl)phthalimide (1.5 g, 5.8 mmole), N,N'-dicyclohexylcarbodiimide (1.2 g, 5.8 mmole) and a catalytic amount of 4-dimethylaminopyridine were dissolved in dry methylene chloride, and the solution was stirred at room temperature for 24 hours. The precipitated crystals were filtered off, and washed with methylene chloride. The mother liquor and filtrate were combined and concentrated under reduced pressure. The residue was purified by silica gel chromatography (chloroform:methanol =10:1). The obtained oil was dissolved in ethanol (50 ml), and hydrazine hydrate (200 mg) was added thereto. The mixture was stirred at room temperature for 3 days. The precipitated crystals were removed by filtration and washed with ethanol. The mother liquor and the washings were combined and concentrated under reduced pressure. The residue was dissolved in dimethylformamide (10 ml). To the solution, caffeic acid (720 mg, 4.0 mmole), 1-hydroxybenzotriazole (540 mg, 4.0 mmole) and N,N'-dicyclohexylcarbodiimide (824 mg, 4.0 mmole) were added, and the resulting mixture were stirred at room temperature for 24 hours. The precipitated crystals were filtered off and washed with dimethylformamide. The mother liquor and the washings were combined and concentrated under reduced pressure. The residue was purified by silica gel column chromatography (chloroform:methanol=5:1). The obtained oil was dissolved in ether (20 ml), and maleic acid ether solution (848 mg/20 ml) was added to the solution. The precipitated crystals were repeatedly washed with ether, and dried at room temperature under reduced pressure to give the compound 12 (1.5 g, yield=51%) described in Table 1.

The structure, melting point, molecular formula and the result of elemental analysis of compound 1 to 13 of the invention prepared by Examples 1 to 3 are shown in Table 1 below.

TABLE 1

| No | Structure | M.P. (°C.) | Chemical Formula | Elemental Analysis C H N |
|---|---|---|---|---|
| 1 | [structure: 3,4-bis(4-methoxyphenyl)-5-[2-(piperidinyl)-1-phenyl-ethoxymethyl]isoxazole · 2 maleate] | 132~135 | $C_{41}H_{53}N_3O_6 \cdot 2C_4H_4O_4$ | 63.95 6.90 4.56<br>64.25 6.71 4.59 |
| 2 | [structure: 3,4-bis(4-methoxyphenyl)-5-[2-(piperidinyl)-1-(4-chlorophenyl)-ethoxymethyl]isoxazole · 2 maleate] | 126~127 | $C_{41}H_{52}N_3O_6Cl \cdot 2C_4H_4O_4$ | 61.74 6.38 4.44<br>61.92 6.36 4.42 |

TABLE 1-continued

| No | Structure | M.P. (°C.) | Chemical Formula | Elemental Analysis C H N |
|---|---|---|---|---|
| 3 | (structure with OCH₃, H₃CO-phenyl groups, isoxazole, CH₂C(=O)-N piperazine-NC₂H₄OH, · CHCO₂H/CHCO₂H) | 155~157 | $C_{25}H_{29}N_3O_5 \cdot C_4H_4O_4$ | 61.13 5.90 7.37<br>61.37 5.86 7.40 |
| 4 | (structure with OCH₃, H₃CO-phenyl groups, isoxazole, CH₂CNH-CH(phenyl)-C(=O)-N piperazine-NC₁₀H₂₁, · CHCO₂H/CHCO₂H) | 110~112.5 | $C_{41}H_{52}N_4O_5 \cdot C_4H_4O_4$ | 67.60 7.17 6.96<br>67.82 7.08 7.03 |

TABLE 1-continued

| No | Structure | M.P. (°C.) | Chemical Formula | Elemental Analysis C H N |
|---|---|---|---|---|
| 5 | (structure with OCH₃, H₃CO, isoxazole, CH₂CNH, phenyl, NC₁₀H₂₁ piperazine) | 124~125.5 | C₄₁H₅₄N₄O₄ | 73.66 8.28 8.39 / 73.84 8.16 8.40 |
| 6 | (structure with OCH₃, H₃CO, isoxazole, CH₂CNH, NC₁₀H₂₀OH piperazine) | 104~105 | C₃₅H₅₀N₄O₅ | 69.02 8.60 9.00 / 69.28 8.31 9.23 |

TABLE 1-continued

| No | Structure | M.P. (°C.) | Chemical Formula | Elemental Analysis C H N |
|---|---|---|---|---|
| 7 | (isoxazole with 3-(4-methoxyphenyl), 4-(4-methoxyphenyl), 5-CH₂CNH-CH(Ph)-CH₂-N(piperazine)-NC₁₀H₂₀OH); O=C | 144~144.5 | $C_{41}H_{54}N_4O_5$ | 71.99 8.08 8.14<br>72.11 7.97 8.20 |
| 8 | (isoxazole with 3-(4-methoxyphenyl), 4-(4-methoxyphenyl), 5-CH₂CNH-CH₂-C(=O)-N(piperazine)-NC₁₀H₂₁); 3/2HCl | 95~97 | $C_{35}H_{48}N_4O_7 \cdot 3/2HCl$ | 63.47 7.96 8.33<br>63.74 7.57 8.50 |

TABLE 1-continued
| No | Structure | M.P. (°C.) | Chemical Formula | Elemental Analysis C H N |
|---|---|---|---|---|
| 9 | 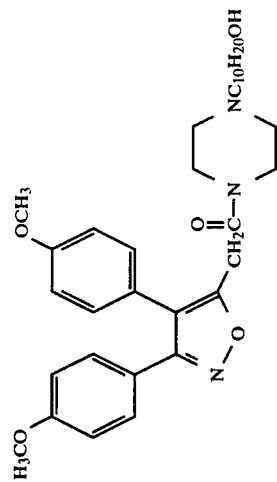 | 155~157 | $C_{33}H_{45}N_3O_5 \cdot C_4H_4O_4$ | 65.29 7.41 6.14<br>65.37 7.27 6.18 |
| 10 | 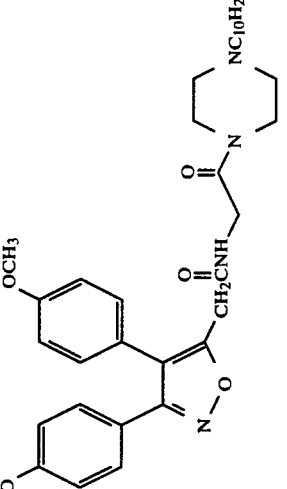 | 76~78 | $C_{35}H_{48}N_4O_6 \cdot (COOH)_2 \cdot 3H_2O$ | 58.23 7.57 7.43<br>58.10 7.38 7.33 |

TABLE 1-continued

| No | Structure | M.P. (°C.) | Chemical Formula | Elemental Analysis C H N |
|---|---|---|---|---|
| 11 | [structure with OCH$_3$, H$_3$CO phenyl groups, isoxazole, CH$_2$C(=O)-N piperazine-NC$_{10}$H$_{20}$COOCH$_3$; CHCO$_2$H / CHCO$_2$H · 1/5H$_2$O] | 179~181 | C$_{35}$H$_{47}$N$_3$O$_6$· C$_4$H$_4$O$_4$· 1/5H$_2$O | 64.55 7.15 5.81 64.57 7.14 5.79 |
| 12 | [structure with OCH$_3$, H$_3$CO phenyl, isoxazole, CH$_2$C(=O)-N piperazine-N-CH$_2$CH$_2$-NHC(=O)-CH=CH-catechol (3,4-dihydroxyphenyl); CHCO$_2$H / CHCO$_2$H · 3/2H$_2$O] | 122~124 | C$_{34}$H$_{36}$N$_4$O$_7$· C$_4$H$_4$O$_4$· 3/2H$_2$O | 60.34 5.76 7.00 60.39 5.73 7.41 |
| 13 | [structure with OCH$_3$, H$_3$CO phenyl, isoxazole, CH$_2$C(=O)-N piperazine-N-pyrimidinyl] | 208 | C$_{27}$H$_{27}$N$_5$O$_4$ | 66.85 5.69 14.29 66.78 5.61 14.42 |

FORMULATION EXAMPLE

Formulation examples using the compounds of the invention are described below.

Formulation Example 1 (Tablets)

Tablets having the following formulation were prepared by the conventional procedure.

| | |
|---|---|
| compound 1 | 100 mg |
| lactose | 47 mg |
| corn starch | 50 mg |
| crystalline cellulose | 50 mg |
| hydroxypropylcellulose | 15 mg |
| talc | 2 mg |
| magnesium stearate | 2 mg |
| ethyl cellulose | 30 mg |
| unsaturated fatty acid glyceride | 2 mg |
| titanium dioxide | 2 mg |
| per one tablet | 300 mg |

Formulation Example 2 (Granules)

Granules having the following formulation were prepared by the conventional procedure.

| | |
|---|---|
| compound 5 | 200 mg |
| mannitol | 540 mg |
| corn starch | 100 mg |
| crystalline cellulose | 100 mg |
| hydroxypropylcellulose | 50 mg |
| talc | 10 mg |
| per one wrapper | 1,000 mg |

Formulation Example 3 (Fine granules)

Fine granules having the following formulation were prepared by the conventional procedure.

| | |
|---|---|
| compound 6 | 200 mg |
| mannitol | 520 mg |
| corn starch | 100 mg |
| crystalline cellulose | 100 mg |
| hydroxypropylcellulose | 70 mg |
| talc | 10 mg |
| per one wrapper | 1,000 mg |

Formulation Example 4 (Capsules)

Capsules having the following formulation were prepared by the conventional procedure.

| | |
|---|---|
| compound 8 | 100 mg |
| lactose | 50 mg |
| corn starch | 47 mg |
| crystalline cellulose | 50 mg |
| talc | 2 mg |
| magnesium stearate | 1 mg |
| per one capsule | 250 mg |

Formulation Example 5 (Syrups)

Syrups having the following formulation were prepared by the conventional procedure.

| | |
|---|---|
| compound 7 | 1 g |
| purified sucrose | 60 g |
| ethyl para-hydroxybenzoate | 5 mg |
| butyl para-hydroxybenzoate | 5 mg |
| flaver | suitable amount |
| coloring agent | suitable amount |
| purified water | suitable amount |
| total amount | 100 ml |

Formulation Example 6 (Injections)

Injections having the following formulation were prepared by the conventional procedure.

| | |
|---|---|
| compound 10 | 100 mg |
| distilled water for injection | sufficient quantity |
| per one ampoule | 2 ml |

Formulation Example 7 (Suppositories)

Suppositories having the following formulation were prepared by the conventional procedure.

| | |
|---|---|
| compound 12 | 100 mg |
| Witepsol W-35 | 1400 mg |
| (registered trademark a mixture of mono-, di- and tri-glyceride of saturated fatty acid consisting of lauric acid to stearic acid; product of DYNAMITE NOBEL Co., Ltd) | |
| per one suppository | 1500 mg |

Pharmacological Tests (1) Cyclooxygenase Inhibitory effect

This assay was carried out by the method described in Russell J. Taylor et al., Biochem. Pharmacol., 25, 2479–2484 (1976).

$^{14}$C-arachidonic acid was reacted with seminal vesicular gland microsomes and the test drugs at various concentrations over a predetermined period of time and the obtained prostaglandin $E_2$ was separated by thin layer chromatography. The radioactivity of prostaglandin $E_2$ was determined by liquid scintillation counter. The $IC_{50}$ values were calculated by the comparison with the radioactivity of the control.

(2) 5-Lipoxygenase inhibitory effect

The assay was carried out by the method described in Kenkichi Ochi et al., J. Biol. Chem., 258, 5754–5758 (1983).

Casein was injected into the abdominal cavity of a guinea pig, and the polymorphonuclear leukocytes were collected and the cytosol fraction was obtained as an enzyme source. $^{14}$C-arachidonic acid was reacted with the enzyme and the test drugs at various concentrations over a predetermined period of time. The obtained 5-hydroxyeicosatetraenoic acid was separated by thin layer chromatography and the radioactivity was determined. The $IC_{50}$ values were calculated by the comparison with the radioactivity of the control.

The table 3 shows the results of the above tests (1) and (2).

| Compound No. | IC$_{50}$ (μM) Cyclooxygenase inhibitory effect | 5-Lipoxygenase inhibitory effect |
| --- | --- | --- |
| 6 | 0.121 | 1.8 |
| 7 | 0.146 | 2.5 |
| 8 | 0.066 | 5.9 |

The results of table 2 shows that the compounds of the present invention potently inhibits a cycloxygenase and a lipoxygenase.

We claim:

1. A isoxazole compound represented by the formula (1):

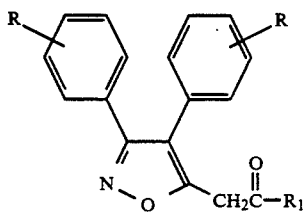

wherein R represents a hydrogen atom or a lower alkoxy group, R$_1$ is a group represented by the formula (2):

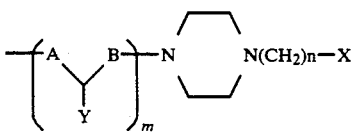

(wherein A represents —NH— or —O—, B represents a methylene group or a carbonyl group, m is 0 or 1, n is an integer of 1 to 12, X represents a hydrogen atom, a hydroxy group or a lower alkoxycarbonyl group, Y represents a phenyl group which can be substituted with one or more halogen atoms, or a hydrogen atom), or R$_1$ is a group represented by the formula (3):

(wherein Z represents a pyrimidinyl group), or R$_1$ is a group represented by the formula (4):

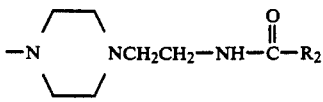

(wherein R$_2$ represents a styryl group which can be substituted with one or more hydroxy groups on the benzene ring thereof); or a pharmaceutically acceptable salt thereof.

2. The isoxazole compound or a pharmaceutically acceptable salt thereof according to claim 1 wherein R is an alkoxy group.

3. The isoxazole compound or a pharmaceutically acceptable salt thereof according to claim 1 wherein R is a methoxy group.

4. The isoxazole compound or a pharmaceutically acceptable salt thereof according to claim 1 wherein R$_1$ is a group represented by the formula (2).

5. The isoxazole compound or a pharmaceutically acceptable salt thereof according to claim 1 wherein R$_1$ is a group represented by the formula (2) wherein A represents —NH— or —O—, B represents a methylene group or a carbonyl group, m is 1, n is an integer of 6 to 12, X represents a hydrogen atom or a hydroxy group, Y represents a phenyl group or a hydrogen atom.

6. The isoxazole compound or a pharmaceutically acceptable salt thereof according to claim 1 wherein R$_1$ is a group represented by the formula (2) wherein A represents —NH—, B represents a methylene group or a carbonyl group, m is 1, n is 10, X represents a hydrogen atom or a hydroxy group, Y represents a phenyl group or a hydrogen atom.

7. The isoxazole compound or a pharmaceutically acceptable salt thereof according to claim 1 wherein R represents a lower alkoxy group, R$_1$ is a group represented by the formula (2) wherein A represents —NH— or —O—, B represents a methylene group or a carbonyl group, m is 1, n is an integer of 6 to 12, X represents a hydrogen atom or a hydroxy group, Y represents a phenyl group or a hydrogen atom.

8. The isoxazole compound or a pharmaceutically acceptable salt thereof according to claim 1 wherein R represents a methoxy group, R$_1$ is a group represented by the formula (2) wherein A represents —NH—, B represents a methylene group or a carbonyl group, m is 1, n is 10, X represents a hydrogen atom or a hydroxy group, Y represents a phenyl group or a hydrogen atom.

9. A composition for inhibiting cyclooxygenase or for inhibiting lipoxygenase comprising an effective amount of a isoxazole compound or a pharmaceutically acceptable salt thereof as defined in claim 1 and a pharmaceutical carrier.

10. A method of inhibiting lipoxygenase which comprises administering to a patient an effective amount of a isoxazole compound or a pharmaceutically acceptable salt thereof as defined in claim 1.

11. A method of inhibiting cyclooxygenase which comprises administering to a patient an effective amount of a isoxazole compound or a pharmaceutically acceptable salt thereof as defined in claim 1.

* * * * *